(12) United States Patent
Katragadda et al.

(10) Patent No.: US 9,566,209 B2
(45) Date of Patent: Feb. 14, 2017

(54) SHOCK WAVE ELECTRODES WITH FLUID HOLES

(71) Applicant: SANUWAVE, INC., Alpharetta, GA (US)

(72) Inventors: Venkata Katragadda, Kennesaw, GA (US); David Booth, Lawrenceville, GA (US); Cary McGhin, Sugar Hill, GA (US); John Jackson, Buford, GA (US); Richard Johnston, Canton, GA (US)

(73) Assignee: SANUWAVE, INC., Suwanee, GA (US)

(*) Notice: Subject to any disclaimer, the term of this patent is extended or adjusted under 35 U.S.C. 154(b) by 0 days.

(21) Appl. No.: 14/929,899

(22) Filed: Nov. 2, 2015

(65) Prior Publication Data

US 2016/0067139 A1 Mar. 10, 2016

Related U.S. Application Data

(62) Division of application No. 13/923,531, filed on Jun. 21, 2013, now Pat. No. 9,198,825.

(60) Provisional application No. 61/663,016, filed on Jun. 22, 2012.

(51) Int. Cl.
*A61B 17/225* (2006.01)
*A61H 23/00* (2006.01)
*G10K 15/04* (2006.01)

(52) U.S. Cl.
CPC .......... *A61H 23/008* (2013.01); *A61B 17/225* (2013.01); *G10K 15/043* (2013.01)

(58) Field of Classification Search
CPC .... A61B 17/225; A61H 23/008; G10K 15/043
See application file for complete search history.

(56) References Cited

U.S. PATENT DOCUMENTS

| | | | | |
|---|---|---|---|---|
| 4,541,848 A * | 9/1985 | Masuda | ................. | H03K 3/537 361/235 |
| 6,217,531 B1 * | 4/2001 | Reitmajer | .............. | G10K 15/06 367/147 |
| 2009/0043300 A1 * | 2/2009 | Reitmajer | ........ | A61B 17/22004 606/41 |
| 2009/0326421 A1 * | 12/2009 | Schwarze | .............. | G10K 15/06 601/4 |
| 2011/0121712 A1 * | 5/2011 | Ma | .......................... | H01T 13/39 313/141 |

FOREIGN PATENT DOCUMENTS

GB 191328369 A * 0/1915 ............... H01T 9/00

* cited by examiner

*Primary Examiner* — Ruth S Smith
(74) *Attorney, Agent, or Firm* — Hunton & Williams LLP

(57) ABSTRACT

Medical devices utilizing shock waves with spark gap electrodes that include fluid holes into the respective electrode cores.

20 Claims, 14 Drawing Sheets

SHOCK WAVE ELECTRODES WITH FLUID HOLES

CROSS-REFERENCE TO RELATED APPLICATIONS

The present application is a divisional application of U.S. application Ser. No. 13/923,531, filed Jun. 21, 2013, now U.S. Pat. No. 9,198,825, which claims the benefit of priority of U.S. Provisional Application No. 61/663,016, filed Jun. 22, 2012, all of which are incorporated herein by reference.

BACKGROUND OF THE INVENTION

Current devices used to generate acoustic shock waves using electro-hydraulic principles typically have a finite life with respect to the electrodes used to generate the shock waves. The primary reason for finite life is the increasing spark gap between the electrodes. As the number of shock waves generated between electrodes increases, the electrode surfaces (tips) facing each other are eroded. As the electrode surfaces erode the distance between the tips grow and the effectiveness of electro-hydraulic shockwave generation is diminished. The finite life of the eroding electrodes can require frequent manual adjustment or replacement of electrodes to maintain an effective spark gap. Thus it is desirable to have an electrode arrangement where the tip design allows a longer functional life and at the same time the electrodes' gap distance is maintained automatically at a substantially constant distance to increase electrode life and reduce the need for manual adjustment or replacement of electrodes.

SUMMARY OF THE INVENTION

The acoustic shock wave produced in embodiments of this invention can be produced through the time-controlled plasma bubble formation and collapse across fixed electrodes placed in a special liquid medium. The formation of the plasma bubble can start with a purely thermal release, which may be generated by the high conductance between the electrodes. The relatively high conductance may produce a flow of electrons between cathode and anode electrodes, which heats the special liquid medium and contributes to plasma formation. The release of electrons and recombination of active atoms generated during high voltage discharge may be catalyzed by the substances present within the special liquid medium that may consist primarily of water with additives such as catalysts, buffer solutions and fine metals to increase conductivity.

During the plasma formation, the gap between the electrodes can be shortened by the leading charged particles, since plasma itself is populated by the charged particles. As the gap shortens, less energy may be needed to continue formation of the plasma arc (discharge) and as the voltage (potential energy) continues to be supplied to the electrodes this may generate a purely thermal release between the particles enclosed by the gap. The driven out electrons are freely mobile in the plasma gas, and the free electrons can ionize different particles on their way through impact resulting in a nuclear chain reaction that begins and forms the plasma channel between the electrodes. If an electron of an ion is caught in the plasma channel, its energy may be converted into oscillation energy (heat) and light (UV-RADIATION). The created energy can continue to heat the plasma and the surrounding environment. The environment adjacent to the plasma region between the two electrodes may heat so fast that water in the special liquid medium may evaporate forming a gas bubble that may grow rapidly and collapse rapidly once the bubble's internal pressure is overcome by the pressure of the surrounding liquid medium and the reduced potential between the two electrodes, thus producing the shock wave. The plasma formation and collapse may occur in less than a microsecond, and the liquid mixture surrounding the electrodes may remain sufficiently stable to sustain creating the next plasma bubble.

In various embodiments the combination of materials in the electrodes, the particular geometry of the electrodes and the composition of the special liquid medium can create the energy versus time reaction needed to produce the plasma bubble, which ultimately may produce the shock wave. In at least one embodiment of the present invention the combination of the electrode material, their geometry and special liquid medium in which the discharge occurs is optimized for at least one of:
  consistency and repeatability of the energy distribution created by the shock wave;
  minimizing misfires (lack of plasma formation);
  reducing the formation of gas bubbles (hydrogen and oxygen) within the special liquid;
  reducing the erosion of the electrodes; and
  maintaining the stability and life of the special liquid medium.

DETAILED DESCRIPTION OF THE INVENTION

Figure 1:
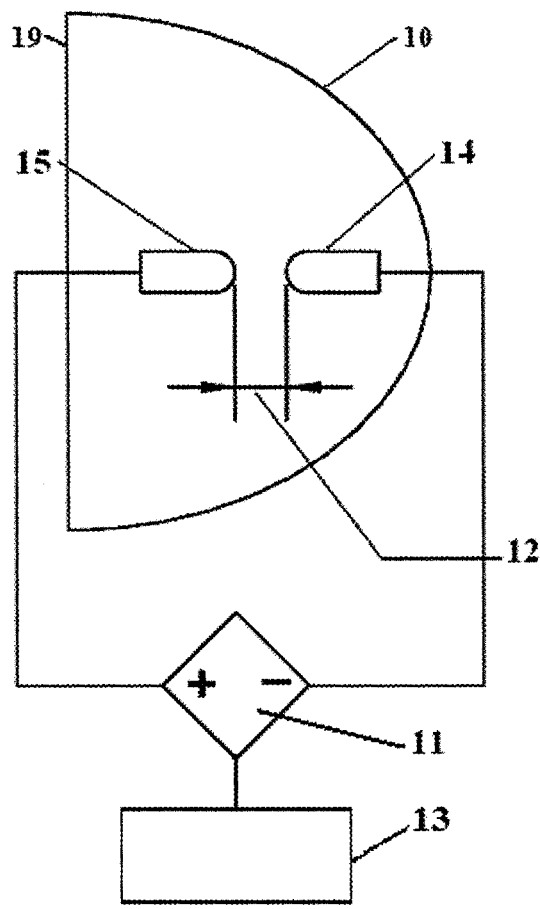
FIG. 1 is a schematic diagram of a conventional applicator treatment head containing two conventional electrodes.

In general, the electrodes in shock wave generation devices for extracorporeal therapy applications are of cylindrical shape and made of special alloys to increase their life expectancy, since in the electrochemical and thermal reaction that occurs during plasma formation some small amount of electrode materials is consumed. This principle is depicted in FIG. 1 of an applicator treatment head 10 containing two electrodes 14 and 15. The gap 12, sometimes referred to as a 'spark gap', between the electrodes 14 and 15 is an important design and manufacturing variable that dictates the energy distribution versus time characteristics of the plasma bubble for producing the shock wave. The produced shock waves can be focused, unfocused, planar, pseudo-planar or radial. This electro-hydraulic principle to create acoustic shock waves as a method of treatment is in use in the medical (lithotripsy, orthopedic use, wound treatment, burns, post-operative treatment, pain treatment, diagnosis, skin and organ transplantation supporting devices, arteriosclerosis treatment), cosmetic (treatment of scars and cellulite) and veterinary (treatment of musculoskeletal disorders) fields.

As the number of shock waves increase, the electrode surfaces facing each other experience erosion and results in increasing the gap 12. As the gap 12 increases from its nominal value, the efficiency and quality of plasma bubble formation decreases adversely affecting the intended use. At this point, the electrodes 14 and 15 must be readjusted for the proper gap.

Electrodes in Special Liquid Medium

The special liquid medium 17, enclosed in the applicator treatment head 10 by membrane 19, in which electrodes are placed must be optimized for the intended application. The special liquid mixture is not only important to the formation of the plasma bubble, but it is also a primary factor to electrode tip erosion. The material of electrode tips (for example, DURATHERM ALLOY) and the composition of the liquid medium surrounding the tips must be considered together, because increased conductivity of the fluid will translate to a higher plasma arcing temperature and will increase erosion of the tip. The other equally important optimization is to reduce the formation of the hydrogen and oxygen gas bubbles (from electrolysis of water). Otherwise the medium will become overwhelmed with gas and cause misfiring of the electrodes or reduce the effectiveness of the shockwave due to large gas bubbles acting as an acoustic insulator for transmitting the shock wave to the body. The water used in the liquid mixture is degassed to an oxygen concentration of 2 mg/liter to minimize oxygen bubble formation. The addition of a hydrogenation catalyst will assist in recombining the hydrogen and/or oxygen back into water. An example of a catalyst for this purpose is palladium which has the ability to absorb hydrogen (1200 ml H2/ml Pd). Metals like magnesium or aluminum will act as oxygen absorbers. A common hydrogenation catalyst in industry is Pd/C consisting of an activated charcoal with palladium, the charcoal acts as a carrier for the palladium and is a good electrical conductor. The large porous structure of the charcoal provides a large surface (>500 m2/g) for supplying the palladium (at the surface of the charcoal) for hydrogenation. The activated charcoal also acts to suspend and distribute the palladium throughout the liquid and increases the conductivity of the water. The other special liquid optimization is to reduce misfires that occur due to poor distribution of ions in the water. If the liquid were comprised solely of the water and catalyst, over time the catalyst settles or clumps and is distributed less uniformly (however it is not a homogenous mixture) throughout the liquid and the initial attempts of plasma formation between the electrodes would not occur. To improve the initial misfiring performance, a buffer is also needed in the liquid to set its pH (increase conductivity) and the effect of a buffer in water will remain stable. The amount of buffer and its pH will affect the erosion of the electrodes, with the more conductive medium allowing more electrode erosion. Also, the conductivity of the liquid affects the plasma formation (i.e., increasing the conductivity reduces the size of the plasma region).

Examples of catalysts that can be utilized:

Nickel, Titanium, Magnesium, Aluminum, Silicon, Silica Gel, PdOH (palladium oxihydrate), $PdCl_2$ (palladium chloride), $Pd/CaCO_3$ (mixture of palladium with $CaCO_3$—calcium carbonate), Pd/Silicate (mixture of palladium with silicate), Pt/C (platinum with active charcoal), Pd/C (palladium with active charcoal), PdO (palladium oxide—hydrated), HDK (pyrogenic silica)

An exemplary catalyst for an embodiment of the invention may be 15 to 30 mg Pd/C/ml water in the special liquid medium.

Examples of conductive agents that can be utilized:

Citrate Buffer pH 4 to 10, Graphite, Charcoal, HCl/THF (hydrochloric acid or hydrochloride salt (HCl) and tetrahydrofuran (THF) solution), HCl/H₂O (hydrochloric acid or hydrochloride salt (HCl) and water (H₂O) solution)

An exemplary conductive agents for an embodiment of the invention may be 4 to 4.5 μl pH6/ml water Examples of colloidal or solubility agents for the catalyst that can be utilized:

Soap, Glycerin, Coupling gel, PEG (polyethylene glycol),

An exemplary colloidal or solubility agents for a catalyst used in an embodiment of the invention may be 15 to 30 μl liquid soap/ml water Test results for different combinations of catalysts and buffers are presented in Table 1 below:

TABLE 1

| Formulation | Performance as Number of Shots Required to Destroy Artificial Stones | Number of Shots where Gas Formation was Observed |
|---|---|---|
| Pd/C 10/50 2.5 g Pd0 0.75 g | 480 | 100,000 |
| Pd/C 10/50 2.5 g Citrate Buffer 0.3 ml | 1,150 | 95,000 |
| Pd/C 10/50 2.5 g PdO 0.1 g | 428 | 93,000 |
| Pd/C 10/50 2.5 g PdO 0.2 g | 595 | 90,000 |
| Pd/C 10/50 3.5 g PdO 0.3 g Citrate Buffer 0.45 ml | 650 | 80,000 |
| Pd/C 10/50 2.5 g Citrate Buffer 0.66 ml | 588 | 65,000 |
| Pd/C 10/50 4 g PdO 0.36 g | 650 | 60,000 |
| Pd/C 10/50 2.5 g, 15-Drop Buffer PH-6 | 760 | 60,000 |
| Pd/C 10/50 2.5 g Pd 0.6 g | 460 | 58,000 |
| Pd/C 10/? 1.5 g | 600 | 56,000 |
| Pd/C 10/50 4 g | 600 | 55,000 |
| PdOH/C 20/50 2.5 g | 620 | 55,000 |
| Pd/C 10/50 2.5 g | 440 | 51,000 |
| Pd/C 10/50 4 g PdO 0.5 g | 700 | 50,000 |
| Pd/C10/50 2.5 g | 480 | 45,000 |
| Pd/C 5/50 2.5 g | 600 | 45,000 |
| Pd/C 10/50 2.5 g | 600 | 42,000 |
| Pd/C 5/50 2.5 g | 740 | 35,000 |
| Pd/C 10/50 2.5 g | 480 | 35,000 |
| PdOH/C 20/50 2 g C 1g | 740 | 17,000 |
| Pd/C 10/50 2.5 g HCl/H₂O | 560 | 8,009 |
| Pd/C 10/50 2.5 g; HCl/THF | 550 | 5,000 |
| Pd/C 10/50 2.5 g PdCl2 0.1 g | 470 | 5,000 |
| Pd/C 10/50 | 540 | 75,000 |

NOTE:
XX/YY denotes the ratio of the different components in the formulation.

The following are optimal liquid mixtures for exemplary embodiments of the special liquid mixture of the invention:

Special Liquid Mixture Embodiment 1 includes a first catalyst with 22 to 28 mg Pd/C/ml of water, a second catalyst with 1.9 to 2 mg Palladium Oxide—Hydrated PdO/ml of water, and a buffer with 4 to 4.5 μl buffer at pH6/ml of water.

Special Liquid Mixture Embodiment 1 includes a first catalyst with 22 to 28 mg Pd/C/ml of water, a second catalyst with 2 to 3 mg HDK/ml of water, and a buffer with 5 to 6 μl buffer at pH10/ml of water Spring-Loaded Electrodes A device generating acoustic shock waves using electrohydraulic principle shown in FIG. 1 has a finite life with respect to generating effective shock waves. The primary reason for finite life is the increasing spark gap 12 between the electrodes, when the electrodes 14 and 15 are energized via the power source 11 controlled by a controller 13.

Figure 2:
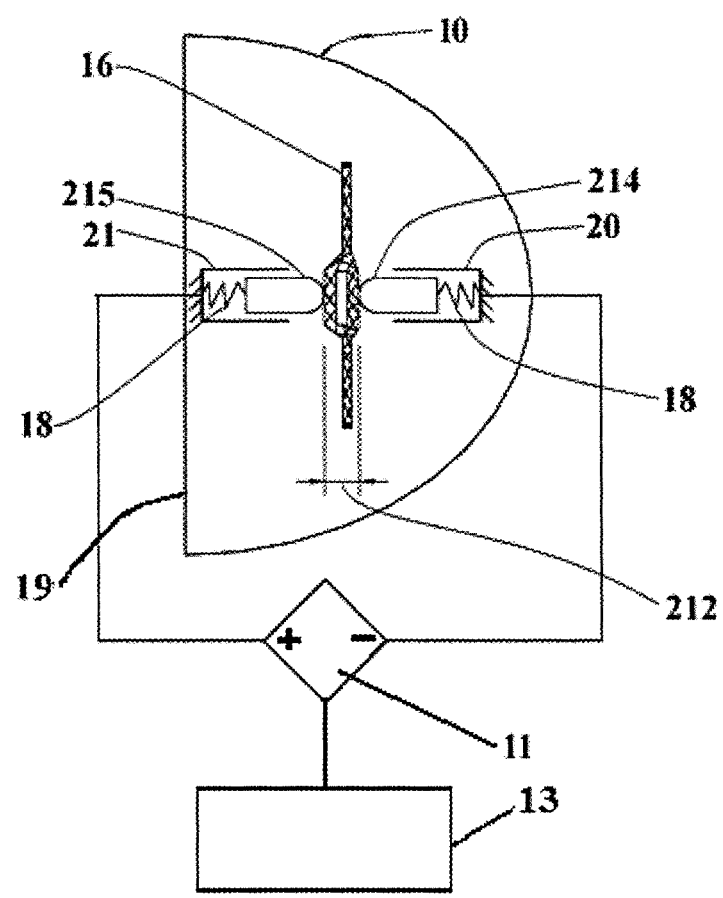
FIG. 2 is a schematic diagram of an embodiment of an applicator treatment head containing two spring loaded electrodes separated by a fine mesh structure to control the gap spacing.

In one embodiment of the invention the electrodes may be arranged where each electrode is supported by a spring-loaded mechanism on one end and a fine mesh structure on the other end as shown in FIG. 2. Electrodes 214 and 215 may be closely encased in cylinders 20 and 21 respectively, and may be supported on one end by a compression spring 18 inside the encasing cylinder. The other end of each electrode may be supported by a rigid porous structure 16. When fully assembled, the distance between the electrode tips 212 is controlled by the rigid porous structure 16. The electrodes 214 and 215 are energized via the controlled power source 11.

As the number of shock waves generated by the device increases, the surfaces at the tips of electrodes 214 and 215 experience erosion. As the erosion increases, each compression spring 18 moves the corresponding electrode 214 and 215 towards the supporting structure 16 thus maintaining a constant distance 212 between the tips of electrodes 214 and 215. Since the distance 212 stays constant, the finite life of the electrodes can be greatly increased providing for less frequent adjustment or replacement of electrodes. This type of electrode arrangement can increase the finite electrode life.

Figure 3:
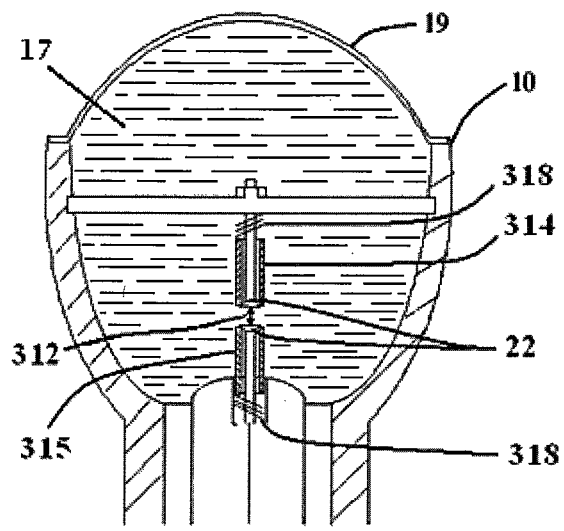
FIG. 3 is a cross-section plan view of an embodiment of an applicator treatment head containing two spring loaded electrodes each held at the proper spacing by their respective hollow non-conductive support.

An alternative embodiment of electrodes supported by springs is shown in FIG. 3. Electrodes 314 and 315 have a hollow center and are supported by a non-conductive members 22 in the center of each electrode and a compression spring 318 on one end. As each electrode 314 and 315 erodes around its circumference, the force from the spring 318 pushes the electrode towards the end stop of the non-conductive member 22 maintaining a nominal 'spark gap' distance 312.

Figure 4:
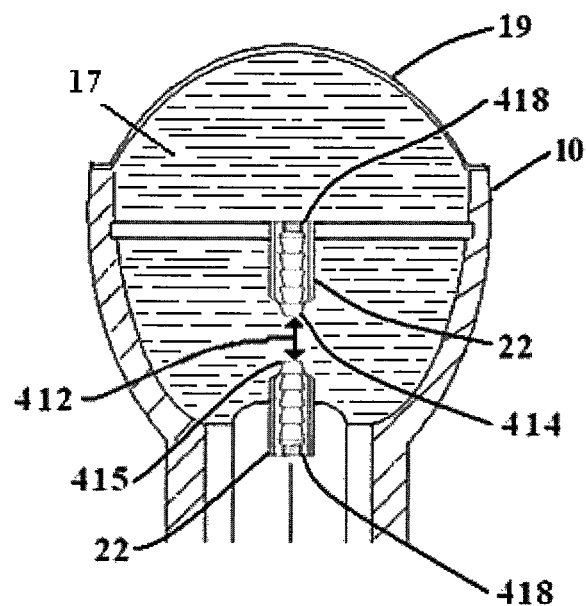
FIG. 4 is a cross-section plan view of an embodiment of an applicator treatment head containing two spring loaded electrodes each held at the proper gap by the step feature in each electrode that aligns with the stop feature in a non-conductive support.

Another alternative embodiment of spring-loaded electrodes is shown in FIG. 4. The profiles of electrodes 414 and 415 have multiple tapered steps in which a hollow non-conductive member 22 encases each electrode 414 and 415 and provides an end stop against the tapered feature of the electrode 414 or 415 under compression by the spring 418 on the other end. As the electrode material erodes the top of the electrode 414 or 415 to a point where the tapered step is removed, the electrode 414 or 415 will be pushed forward by the spring and stop at the next tapered step. Once this happens the nominal 'spark gap' distance 412 is restored.

Figure 5:
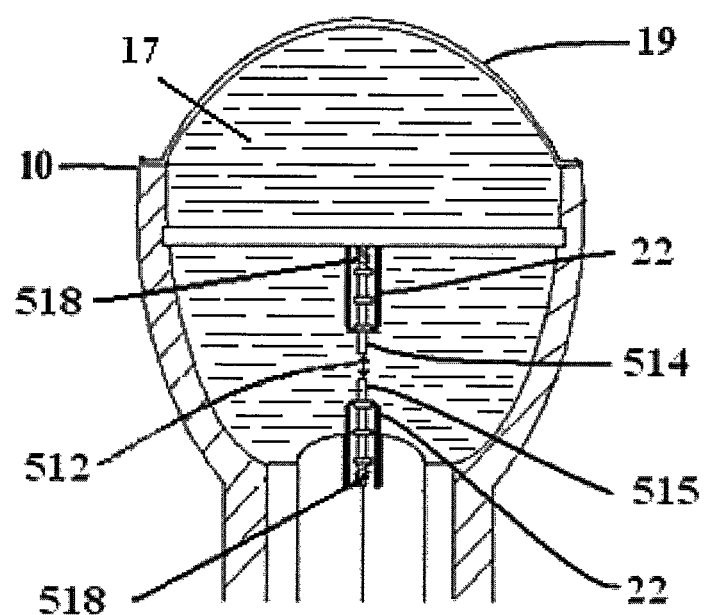
FIG. 5 is a cross-section plan view of an embodiment of an applicator treatment head containing two spring loaded electrodes each held at the proper gap by a detent feature in each electrode.

A different embodiment for the electrode geometry that utilizes similar in function to FIG. 4 is shown in FIG. 5. The profile of each electrode 514 and 515 has multiple detents or steps in which a hollow non-conductive member 22 encases each electrode 514 and 515 and provides an end stop against the step feature of the electrodes 514 and 515. Once the electrode material erodes the step, the electrode 514 or 515 will be pushed forward by the spring 518 and stop at the next step. Once this happens the nominal 'spark gap' distance 512 is restored.

Ring Shaped Electrodes

Figure 6A:
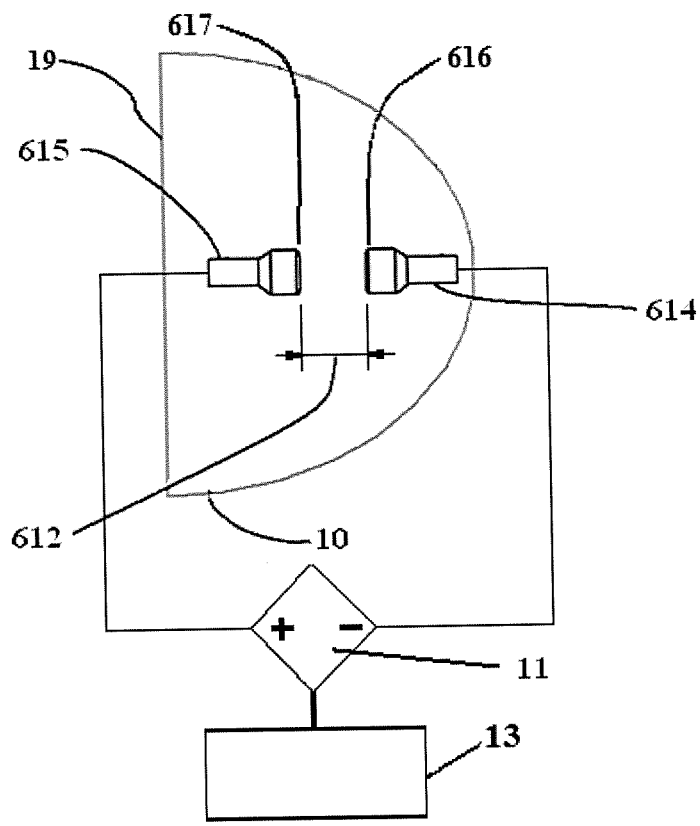
FIG. 6A is a schematic diagram of an embodiment of an applicator treatment head containing two electrodes each designed as a cylindrical ring to increase the surface area of the discharge so that the electrode wear is reduced.
Figure 6B:
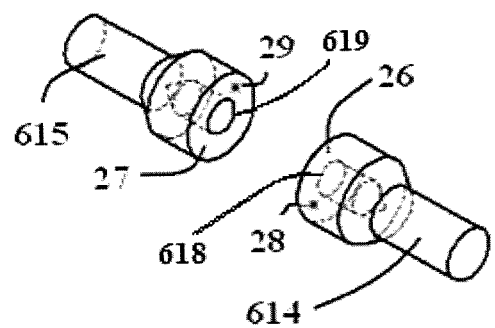
FIG. 6B is a wireframe perspective view of the electrodes described in FIG. 6A.

As shown in FIGS. 6A and 6B another embodiment where electrodes 614 and 615 may have cylindrical ring-shaped parallel planar surfaces 26 and 27 respectively at their respective tips 616 and 617. The outer diameters of the cylindrical ring-shaped parallel planar surfaces 26 and 27 may be greater than the diameter of the base of the electrodes 614 and 615. The electrode shape shown in FIG. 6B provides for larger tip surface areas of the cylindrical ring-shaped parallel planar surfaces 26 and 27 for discharge to occur when electrodes 614 and 615 are energized by the power provided by the controlled power source 11 controlled by a controller 13. Electrodes 614 and 615 may include a bore 618 and 619 in the center of each electrode to allow heat to conduct more efficiently to the special liquid medium surrounding the electrodes.

The electrical discharge, when the design shown in FIGS. 6A and 6B is powered from the controlled power source 11, can occur across one or multiple points 28 and 29 on the cylindrical ring-shaped parallel planar surfaces 26 and 27, respectively. The location of discharge points 28 and 29 is dictated by path of least resistance to electrical discharge provided by the controlled power source 11. As the number of voltage discharges increase, the location of 28 and 29 will change because the surfaces 26 and 27 experience localized material erosion. The gap 612 across the electrodes shown in FIG. 6A decreases at a lower rate than that of FIG. 1 due to a larger electrode tip surface area, which increases heat dissipation and provides a random change in the discharge path. The outer diameter on the ring shaped end of the electrode cannot be too large as that it will cause incorrect focusing of acoustic shock waves.

Modified Ring Shaped Electrodes

Figure 7A:
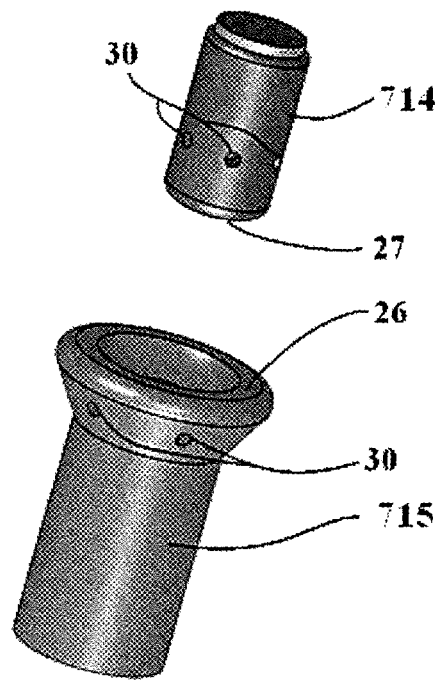
FIG. 7A is a perspective view of an embodiment of two electrodes, each designed as a cylindrical ring having a large surface area and each having multiple radial holes that facilitate fluid circulation to the core of the electrodes, for improved heat dissipation from the electrodes.
Figure 7B:
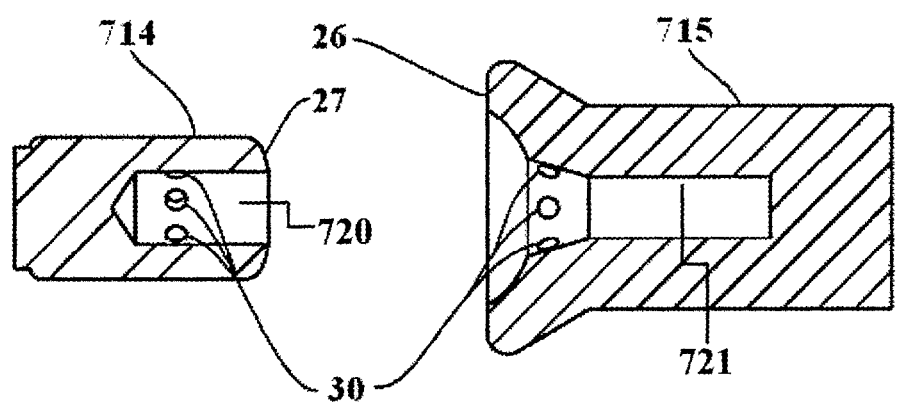
FIG. 7B is a cross-section plan view of the electrodes described in FIG. 7A.

The electrode geometry shown in FIGS. 6A and 6B may be further modified as shown in FIG. 7A and FIG. 7B. The ratio of electrode tip surfaces 26 and 27 is greater than one (26:27>1). This can be beneficial to embodiments of the electrodes because the surface of the anode electrode 26 wears faster than the surface of the cathode electrode 27 and different dimensions may allow a uniform gap adjustment from both ends. Both electrodes 714 and 715 have multiple radial holes 30 that facilitate fluid circulation to the cores 720 and 721 of the electrodes. Better fluid circulation may improve heat dissipation from the electrodes 714 and 715 into the special liquid medium.

Complementary Profile Electrodes

Figure 8A:
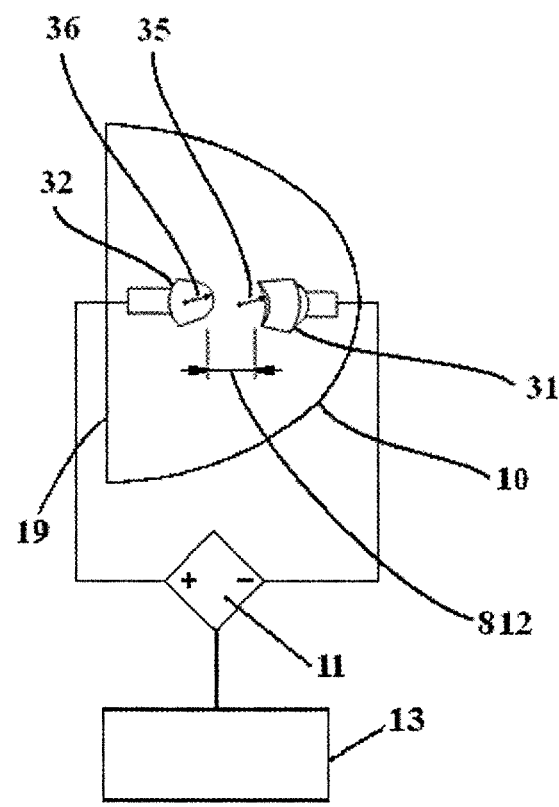
FIG. 8A is a schematic diagram of an embodiment of an applicator treatment head containing two electrodes having a mirrored or complimentary tip profile with equal radiuses to increase the electrode life.
Figure 8B:
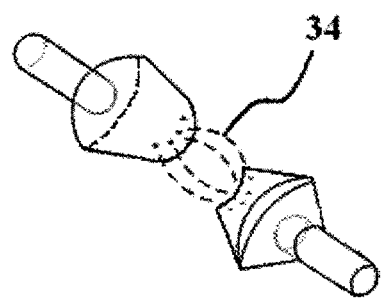
FIG. 8B is a wireframe perspective view of the electrodes described in FIG. 8A.

An alternate embodiment for the shape of the electrodes shown in FIGS. 8A and 8B will provide longer electrode life due to the complementary tip shape of the electrodes. Electrode 31 has a convex tip profile and electrode 32 has a concave tip profile, which are complementary to one another with convex radius 35 being equal to concave radius 36. The complementary tip profiles create equidistant electric field lines 34 for setting up an equipotential electric field across the gap 812, when the electrodes 31 and 32 are powered by the controlled power source 11. The gap 812 across the electrodes 31 and 32 may decrease at a lower rate than that of prior art the electrodes 14 and 15 of FIG. 1 due to the equipotential electric field lines 34 and the larger tip surface area. This is different when compared to the prior art electrodes 14 and 15 of FIG. 1 whose point to point gap 12 varies over the tip surface yielding electric field lines of varying intensity between the electrodes that is further exacerbated by tip erosion.

Concentric Coplanar Electrodes with Cylindrical Spark Gap

Figure 9A:
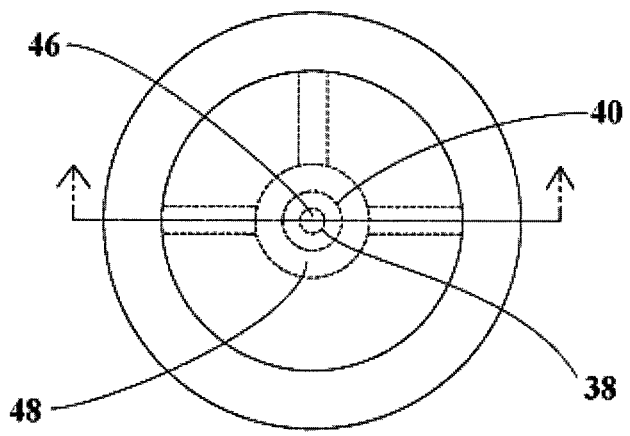
FIG. 9A is a top plan view of an embodiment of the applicator treatment head containing two electrodes, center electrode cylinder and an outer electrode ring, that are concentric and coplanar so that the electrodes wear more evenly.
Figure 9B:
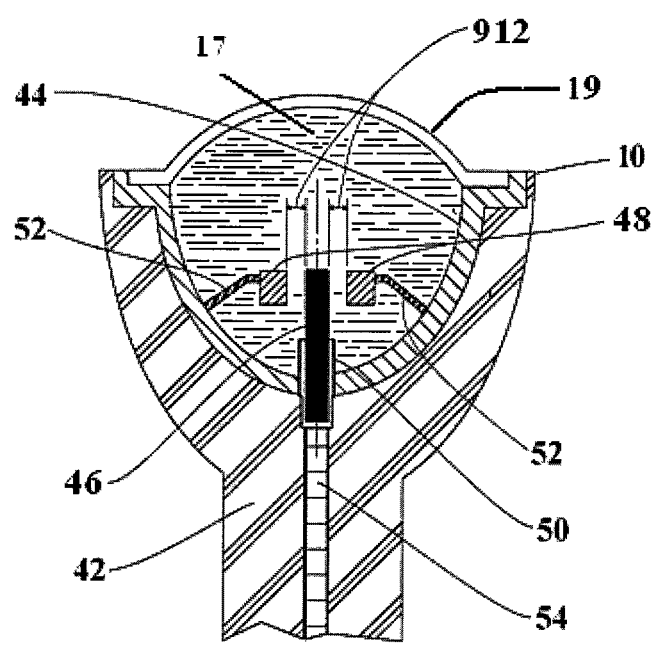
FIG. 9B is a cross-section plan view of the applicator treatment head described in FIG. 9A.

An alternative embodiment to extend the life of the electrodes is shown in FIGS. 9A and 9B. By distributing the spark gap radially along the entire circular/cylindrical gap 912 region erosion of the material of electrodes 46 and 48 should be minimized. If any portion of the material 38 of the inner electrode 46 or the material 40 of the outer electrode 48 become eroded, the gap will be maintained by the other positions around the circumference of the electrode cylinders 46 and 48 allowing continued firing and a much longer useful life than current single/point gap designs as previously shown in prior art FIG. 1.

FIG. 9B illustrates the cylindrical spark gap arrangement inside the applicator body 42. The top view of the spark gap assembly, shown in FIG. 9A, contains an inner electrode 46, a center electrode cylinder 50, and an outer electrode ring 48. Both electrodes may be mounted to the applicator body 42 and conductive reflector 44 of FIG. 9B via snap-on locking pins or other mounting mechanism, which allows precise positioning of the electrodes. Power to the inner electrode 46 of FIG. 9B is supplied via a wire cable 54 whereas the outer electrode is connected to the mounting struts 52 that provides a return path to ground via a conductive reflector 44.

Multiple Electrode Tips

Figure 10:
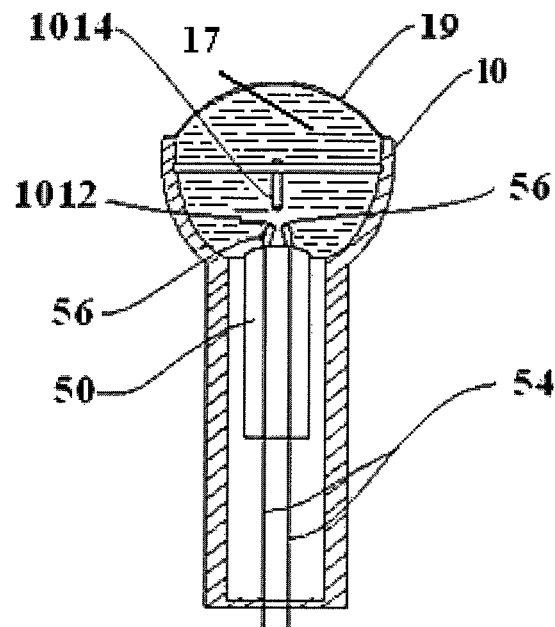
FIG. 10 is a cross-section plan view of an embodiment of an applicator treatment head containing multiple electrode tips for the Anode, which typically wears faster than the Cathode that is grounded to the metal reflector.

In general, referring back to FIG. 1, the electrode 14 may have the less mass is designated as the cathode, and experiences faster erosion compared to the erosion by the other electrode 15, the anode. In one embodiment, as shown in FIG. 10, increasing the mass of the cathode electrode 1014 along with utilizing multiple anode tips 56 can be arranged such that electrical discharge takes place alternatively across the cathode 1014 and each Anode 56. This configuration effectively decreases the net electrode erosion resulting in reducing the rate of spark gap 1012 increase. Power to each anode tip 56 is supplied through separate wire cables 54 so that each anode tip 56 can be alternately powered as another means of controlling tip erosion. In alternative embodiment of this design the cathode electrode may consist of multiple tips as opposed to the anode electrode.

Position Adjustable Electrodes

Figure 11:
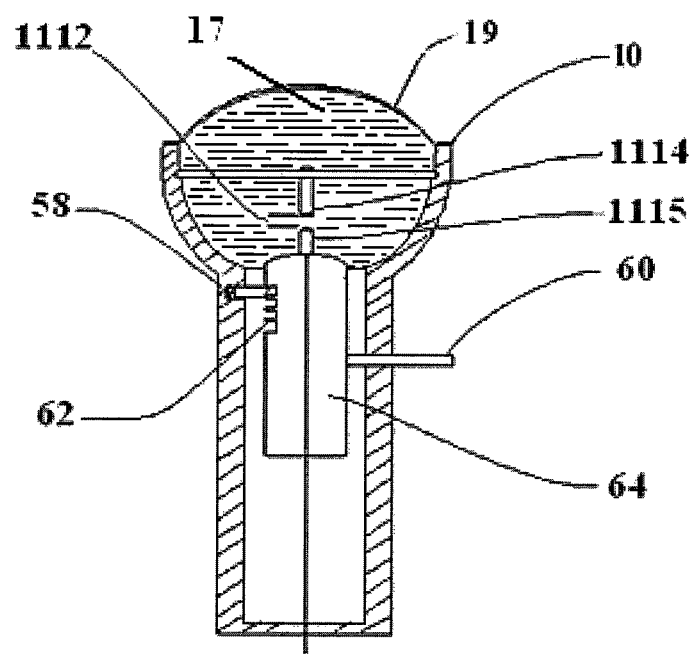
FIG. 11 is a cross-section plan view of an embodiment of an applicator treatment head with a manual adjustment mechanism using a handle for setting the electrode gap.

The shock wave device may include a user adjustable electrode positioning device as shown in FIG. 11. A user adjustable electrode positioning device can increase the overall useful life of the electrodes. In one embodiment electrode 1115 is assembled such that user can adjust the 'spark gap' 1112 distance. Electrode 1115 is assembled to a movable mechanism 64 interfacing with a spring-loaded one directional latch 58 and a position adjustment handle 60. The interaction between the latch 58 and detents 62 of the movable electrode supporting body 64 allows positioning the electrode 1115 at a nominal location. The user can move the position adjustment handle 60 until both electrodes 1114 and 1115 come in contact with each other and then move the handle 60 in the opposite direction until the latch 58 engages into the detent 62. This user performed operation may reset the 'spark gap' distance 1112 to a nominal value.

Figure 12:
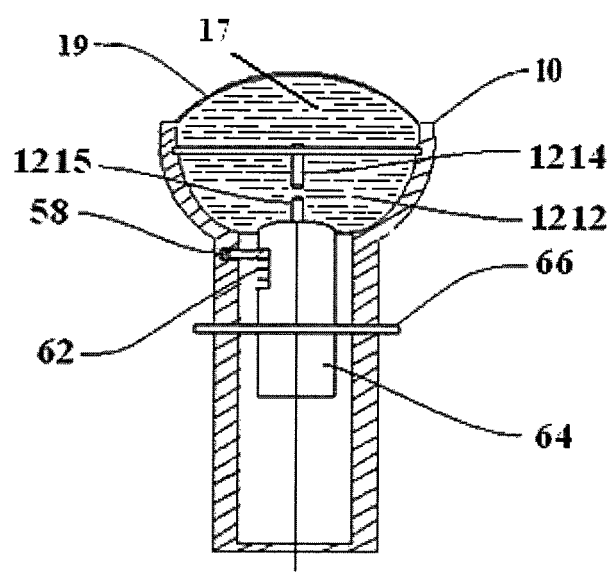
FIG. 12 is a cross-section plan view of an embodiment of an applicator treatment head with a manual adjustment mechanism using a threaded nut for setting the electrode gap.

Alternatively, in another embodiment shown in FIG. 12 a user adjustable positioning nut 66 that is integrated with the moveable electrode supporting body 64 can be adjusted to set the 'spark gap' distance 1212 to a nominal value. The user can turn the adjustable positioning nut 66 until both electrodes 1214 and 1215 come in contact with each other and then turn the positioning nut 66 in the opposite direction until the spring loaded latch 58 engages into the detent 62.

Figure 13A:
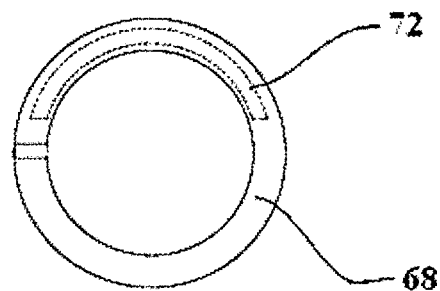
FIG. 13A is a top plan view of an embodiment of an applicator treatment head with a manual adjustment feature embodied in a rotating membrane assembly that adjusts one electrode toward the other.
Figure 13B:
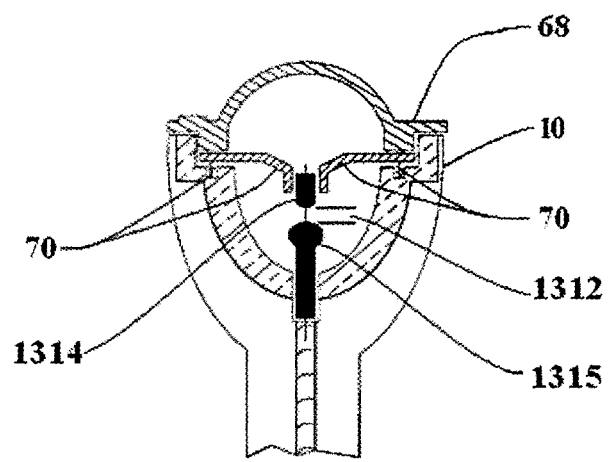
FIG. 13B is a cross-section plan view of the applicator treatment head described in FIG. 13A.

In another arrangement shown in the FIGS. 13A and 13B, electrode 1314 is assembled to a spring-loaded mechanical member 70. The mechanical member 70 is captured by a hard plastic membrane 68. The hard plastic membrane 68 has a ramp geometry 72, shown in top view FIG. 13A, on part of its surface such that when rotated will force the electrode 1314 towards the electrode 1315. This user performed operation will restore the nominal 'spark gap' distance 1312.

Figure 14:
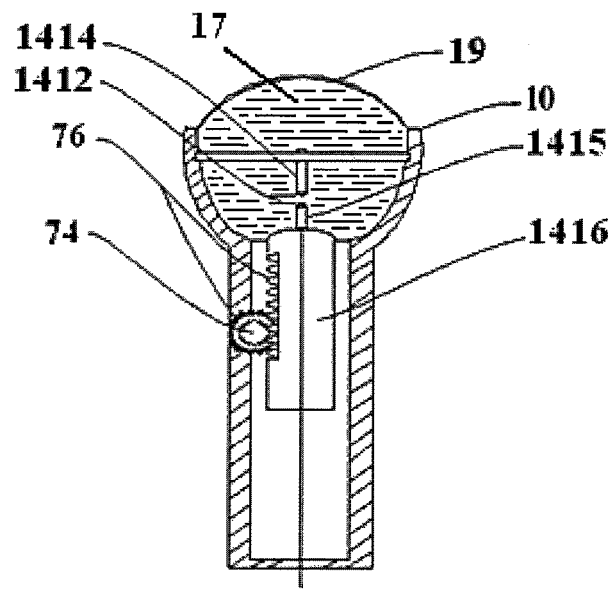
FIG. 14 is a cross-section plan view of an embodiment of an applicator treatment head with a motor controlled adjustment mechanism for adjusting the electrode gap distance.

In a further embodiment, the spark gap distance 1412 can be adjusted automatically through a mechanical drive train 76 coupled to a stepper motor 74 as shown in FIG. 14. The drive train 76 is coupled with the electrode supporting body 1416 so that as the stepper motor 74 rotates the electrode 1415 will move either toward or away from the opposing electrode 1414 based on direction of motor rotation. A control system (not shown) for stepper motor 74 can be used to adjust the electrode 1415 by first closing the gap 1412 and then moving the electrode 1415 in the opposite direction to a fixed distance. Alternatively, the stepper motor 74 can be controlled based on automatically estimating the spark gap distance 1412. A method to automatically estimate the spark gap distance 1412 is shown in FIG. 15 and described later in this document.

Spark Gap Sensing and Compensating System

Figure 15:
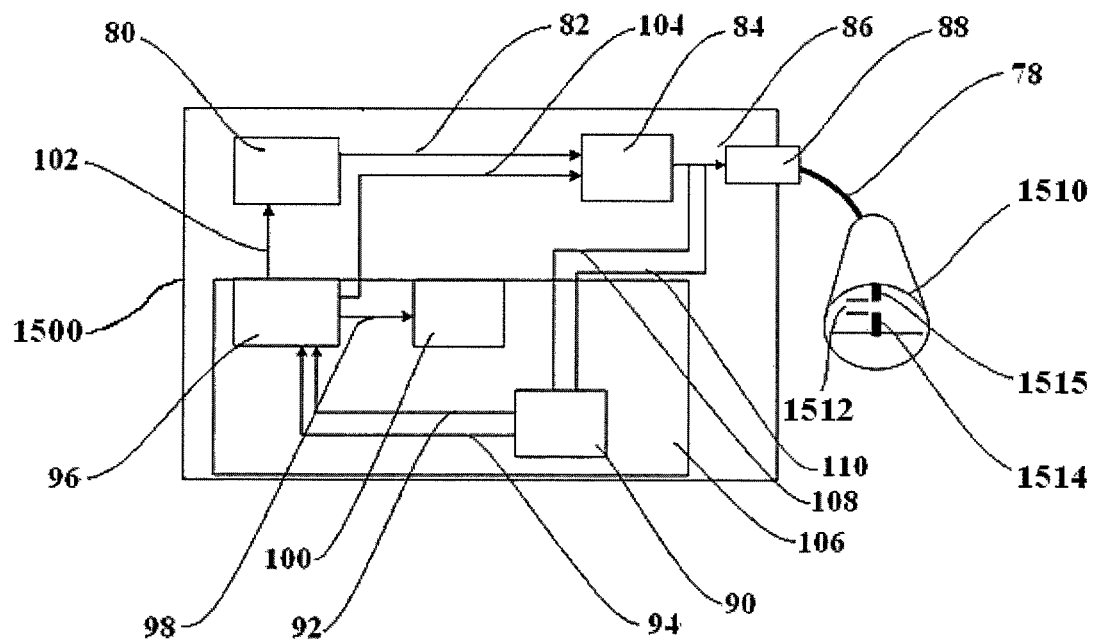
FIG. 15 is a diagram of an embodiment of a control system used to determine the electrode gap distance of various embodiments of the invention.

An embodiment for a system to sense the gap distance 1512 is shown in FIG. 15. A control system 1500 that may also be responsible for generating the high voltage applied between the electrodes 1514 and 1515, can utilize different controls of a high voltage generator 80 and high voltage switch 84 to apply a specific voltage impulse or multiple voltage impulses at a much lower voltage to the electrodes 1514 and 1515. Using the relationship of impulse voltage 108 to impulse current 110 in the applied signal to the treatment head 1510, the electrode gap 1512 of the applicator treatment head 1510 can be determined. This may be performed prior to starting treatment, during a treatment session or in between treatment sessions. If the gap 1512 increases significantly the control system may alert the user. In a further embodiment, the gap measurement system can be integrated with a treatment head with the manually or automatically adjustable electrode gap shock wave applicators, which were described earlier in this specification.

In the case of a shock wave device with manually adjustable electrodes the user is provided an external means to adjust the gap distance of the applicator treatment head as described in FIGS. 11-13B, and may be provided with a viewing aid displayed on the control system's display 100. The adjustment is made by the user to set the optimum distance. The user may be further assisted with the manual adjustment of the electrode gap distance 1512 by instructions that may be shown on display 100 instructing the user to adjust the tips until they touch followed by using the adjustment in the opposite direction a specific number of turns. Another method of gap adjustment may use the equivalent capacitance measurement by the Gap Sensing Interface 106 of FIG. 15 and FIG. 16, which is described later in this specification.

Figure 16:
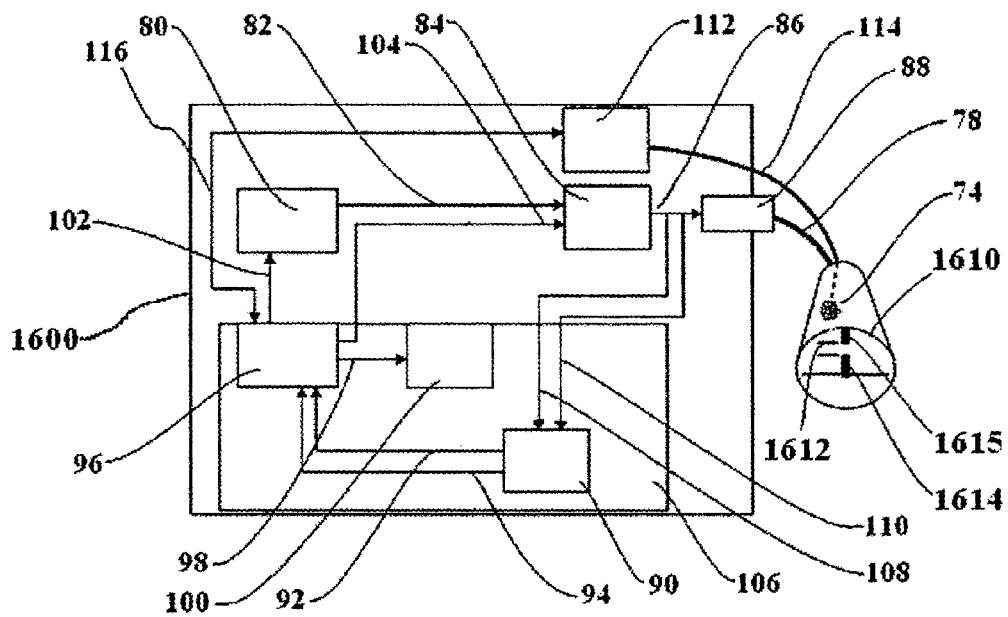
FIG. 16 is a diagram describing an embodiment of the control system used to determine the electrode gap distance and control the motor of FIG. 14 to adjust the electrode gap.

In an embodiment where the adjustment is automated, the control system 1600 may be coupled to a shock wave device with an electromechanical drive 76 as depicted in FIG. 14 and a motor drive and control system 112, as shown in FIG. 16, to set the electrode gap with the feedback from the Gap Sensing Interface 106, or can be based off a position encoding of the electrode tips that is integrated into the stepper motor 74. Using an embodiment with the position encoded electrode tips, the stepper motor 74 would be commanded via the motor control 112 and position sensing signal 116 from the microcontroller 96 to move the adjustable electrode until it touches the tip of the other electrode, this is detected using the feedback from the Gap Sensing Interface 106. After electrodes 1614 and 1615 are in contact with each other the stepper motor 74 would be controlled to move the adjustable electrode in the opposite direction to the nominal gap distance 1612. Controlling the stepper motor 74 rotation occurs by the motor control and position sensing signal 116 from the microcontroller 96 to the motor driver 112 and the motor drive and sensing interface cable 114.

In both FIG. 15 and FIG. 16, microcontroller 96 can be responsible for controlling the high voltage to the treatment head 1510 and 1610 respectively, using the Generator Enable signal 102 and the HV Switch Enable 104 that will provide the impulse voltage via the HV Connector 88 and HV Cable 78 to the treatment head 1510 or 1610. The Gap Sensing Interface 106 measures the impulse voltage and current to the treatment head 1510 or 1610 using the Voltage and Current Signal Processor 90, the Microcontroller 96, and the Display 100.

The microcontroller 96 may initiate the measurement of the electrode gap 1512 or 1612 by generating a particular impulse voltage or combination of impulse voltages from the HV Generator 80 using the Microcontroller interface Generator Control 102. The voltage generated by the HV Generator 80 would be less than normally used to create a shock wave. The HV Switch 84 is enabled to apply the Generator Output 82 to the treatment head 10 by the control signal HV Switch Enable 104. The impulse voltage and impulse current on the output 86 of the HV Switch 84 is sensed by a Voltage and Current Signal Processor 90. The Voltage and Current Signal Processor 90 converts the impulse voltage and impulse current applied to the treatment head into a digital form 92 and 94 respectively, which is processed by the Microcontroller 96. The Microcontroller software determines the electrode gap distance 1512 or 1612 through the derivation of the Equivalent Capacitance ("EC") of the treatment head.

The microcontroller 96 may derive the EC by correlating it to the standard electrical capacitance formula for a parallel plate capacitor as shown below:

$$EC \approx \in_r (A_{tip}/d_{gap})  \quad \text{Equation 1}$$

The formula of Equation 1 can be replaced by other mathematical models that may be a more complex model of the EC for the treatment head. In the simplest case of Equation 1, "$\in_r$" is the dielectric value of the special liquid medium within the treatment head. The electrode tip surface area ("$A_{tip}$") can be considered constant as it is less of a factor compared to the electrode gap distance ("$d_{gap}$") in calculating the EC, and the dielectric value can also be assumed to be constant, so the gap distance can be derived by knowing the EC. The microcontroller will measure the voltage ("V") and current ("I") applied to the treatment head and from that derive EC using the formula:

$$EC = \frac{\int I \cdot dt}{V} \quad \text{Equation 2}$$

$$d_{gap} \approx \frac{\varepsilon_r \cdot A_{tip}}{\frac{\int I \cdot dt}{V}} \quad \text{Equation 3}$$

In Equation 3, the microcontroller 96 may integrate the measured current ("I") applied to the treatment head or can measure current decay over a finite period, from that the charge stored in the capacitance of the electrodes is determined which is required to derive the EC. In conclusion, the microcontroller can measure the voltage ("V") and current ("I") applied to the treatment head to monitor the distance between the electrodes.

Empirical Electrode Life Span Estimation

Figure 17:
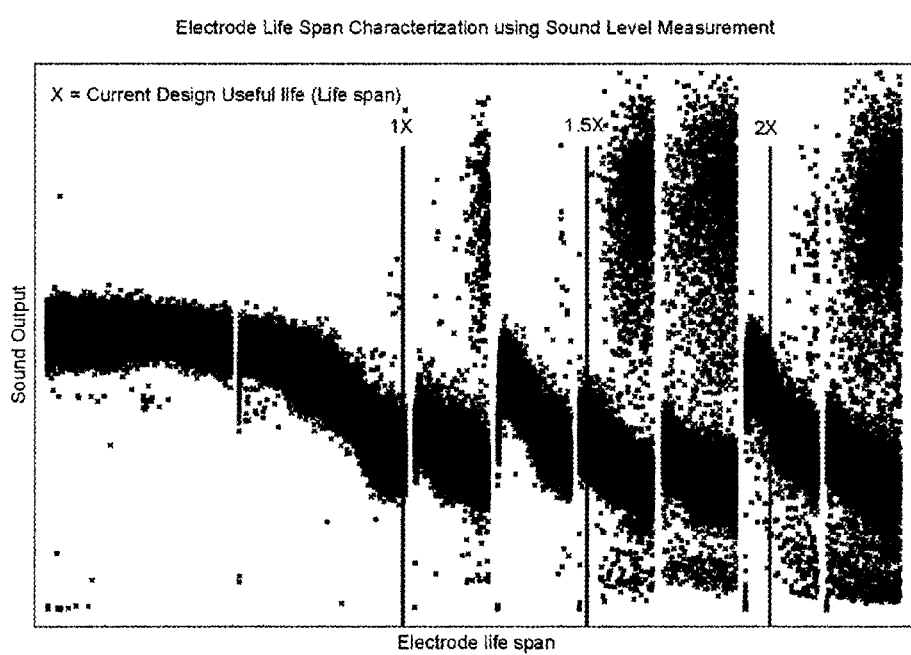
FIG. 17 is a graph plot of test results for the sound output level with electrode wear using the conventional prior art electrode design described in FIG. 1.

Acoustic shock wave pulses produce a distinct audible sound that can be measured using a Sound Pressure Level meter. The measured sound level of continuous pulses falls within a tight range when the 'spark gap' is within the design limits. As the 'spark gap' distance increases, the measured sound level from continuous pulses starts to diverge from the tight range described earlier. This is an indication of inconsistent plasma bubble formation. FIG. 17 shows empirical data for a 'spark gap' of the prior art shock wave device of FIG. 1. The data shows a clear divergence of sound level measurements as the number of continuous pulses (life span) increases. The divergence of sound level data can be delayed by changing the geometry of electrode tips as described in this specification (i.e., the spark gap useful lifespan can be increased).

Figure 18:
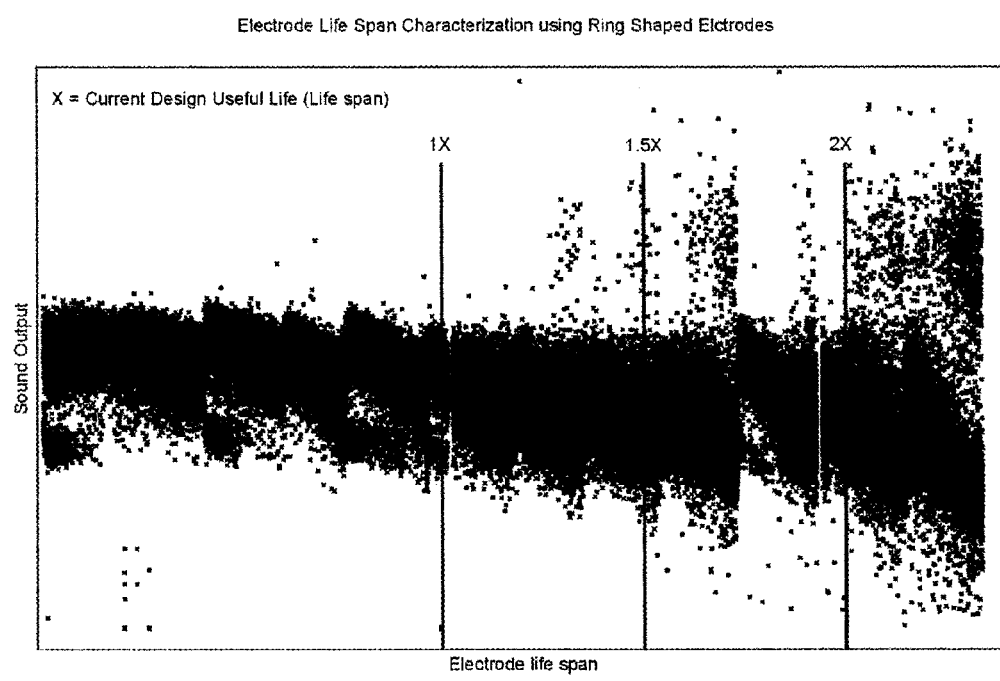
FIG. 18 is a graph plot of test results for the sound output level with electrode wear using the electrodes described in FIGS. 6A and 6B.

When a combination of optimized catalysts and buffers combined with tip shape and material is used, in accordance with embodiments described in this specification, the data shows an increased longevity of the applicators' lifespan as can be seen in FIG. 18. This suggests that for medical applications, where the spark generating electrodes are used in a non-consumable fluid that incorporates optimal amounts of catalysts, buffers and conductive particles and are combined with optimal materials and shape for the electrodes as shown in the various embodiments of the invention, the longevity of the shock waves applicators can be increased.

The foregoing description of the exemplary embodiments of the invention has been presented only for the purposes of illustration and description and is not intended to be exhaustive or to limit the invention to the precise forms disclosed. Many modifications, combinations and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope.

Accordingly, the scope of the present invention is defined by the appended claims rather than the foregoing description and the exemplary embodiments described therein.

What is claimed is:

1. A shock wave applicator device, comprising:
an applicator head including an enclosure sealed by a membrane;
a liquid mixture including water with a buffer and one or more catalysts disposed within the enclosure;
a first electrode having a ring-shaped first tip surface disposed in the liquid mixture in the enclosure and the first electrode including a plurality of holes into a first core of the first electrode, wherein said first core is open to a central opening in the ring-shaped first tip surface;
a second electrode having a ring-shaped second tip surface disposed in the liquid mixture in the enclosure and the second electrode including a plurality of holes into a second core of the second electrode, wherein said second core is open to a central opening in the ring-shaped second tip surface, and wherein the second tip surface of the second electrode is spaced apart from the first tip surface of the first electrode by a spark gap distance, and wherein tip surface dimensions of the second electrode tip surface are larger than tip surface dimensions of the first electrode; and
a controller and a power source coupled to the first and second electrodes.

2. The shock wave applicator device of claim 1, wherein the first electrode is cylindrical.

3. The shockwave applicator of claim 2, wherein the plurality of holes of the first electrode are radial holes of the first electrode and the plurality of holes of the second electrode are radial holes of the second electrode.

4. The shockwave applicator device of claim 3, wherein the one or more catalysts includes a first catalyst comprising 22 to 28 milligrams palladium with active charcoal per milliliter of water and a second catalyst comprising 1.9 to 2 milligrams palladium oxide per milliliter of water, and wherein the buffer has a pH of 6 and is in an amount of 4 to 4.5 microliters of buffer per milliliter of water.

5. The shockwave applicator device of claim 3, wherein the one or more catalysts includes a first catalyst comprising 22 to 28 milligrams palladium with active charcoal per milliliter of water and a second catalyst comprising 2 to 3 milligrams pyrogenic silica per milliliter of water, and wherein the buffer has a pH of 10 and is in an amount of 5 to 6 microliters of buffer per milliliter of water.

6. The shockwave applicator device of claim 3, further comprising a stepper motor coupled to at least one of the electrodes, wherein the stepper motor is actuated by the controller to incrementally adjust the spark gap distance between the electrodes.

7. The shockwave applicator device of claim 3, further comprising a handle coupled to at least one of the first electrode and second electrode for manual adjustment of the spark gap distance between the electrodes.

8. The shockwave applicator device of claim 3, wherein the controller determines spark gap distance between the electrodes by calculation of equivalent capacitance of the applicator head.

9. The shockwave applicator device of claim 2, further comprising a handle coupled to at least one of the first electrode and second electrode for manual adjustment of the spark gap distance between the electrodes.

10. The shockwave applicator device of claim 2, further comprising a display operatively coupled to the controller and providing viewable instructions for adjustment of the spark gap distance between the electrodes.

11. The shockwave applicator device of claim 2, wherein the controller determines spark gap distance between the electrodes by calculation of equivalent capacitance of the applicator head.

12. The shockwave applicator device of claim 11, further comprising a stepper motor coupled to at least one of the electrodes, wherein the stepper motor is actuated by the controller to incrementally adjust the spark gap distance between the electrodes.

13. The shockwave applicator device of claim 2, further comprising a stepper motor coupled to at least one of the electrodes, wherein the stepper motor is actuated by the controller to incrementally adjust the spark gap distance between the electrodes.

14. The shockwave applicator of claim 1, wherein the plurality of holes of the first electrode are radial holes of the first electrode and the plurality of holes of the second electrode are radial holes of the second electrode.

15. The shockwave applicator device of claim 1, wherein the one or more catalysts includes a first catalyst comprising 22 to 28 milligrams palladium with active charcoal per milliliter of water and a second catalyst comprising 1.9 to 2 milligrams palladium oxide per milliliter of water, and wherein the buffer has a pH of 6 and is in an amount of 4 to 4.5 microliters of buffer per milliliter of water.

16. The shockwave applicator device of claim 1, wherein the one or more catalysts includes a first catalyst comprising 22 to 28 milligrams palladium with active charcoal per milliliter of water and a second catalyst comprising 2 to 3 milligrams pyrogenic silica per milliliter of water, and wherein the buffer has a pH of 10 and is in an amount of 5 to 6 microliters of buffer per milliliter of water.

17. The shockwave applicator device of claim 1, further comprising a handle coupled to at least one of the first electrode and second electrode for manual adjustment of the spark gap distance between the electrodes.

18. The shockwave applicator device of claim 1, further comprising a display operatively coupled to the controller and providing viewable instructions for adjustment of the spark gap distance between the electrodes.

19. The shockwave applicator device of claim 1, wherein the controller determines the spark gap distance between the electrodes by calculation of equivalent capacitance of the applicator head.

20. The shockwave applicator device of claim 1, further comprising a stepper motor coupled to at least one of the electrodes, wherein the stepper motor is actuated by the controller to incrementally adjust the spark gap distance between the electrodes.

* * * * *